US005643892A

United States Patent [19]
Striker et al.

[11] Patent Number: 5,643,892
[45] Date of Patent: Jul. 1, 1997

[54] METHOD OF TREATING CHRONIC PROGRESSIVE VASCULAR DISEASES

[75] Inventors: Gary E. Striker; Liliane J. Striker, both of Bethesda, Md.; Fred P. Sherman, Hollywood, Fla.

[73] Assignees: Baker Norton Pharmaceuticals, Inc., Miami, Fla.; The United States of America as represented by the Department of Health and Human Services, Washington, D.C.

[21] Appl. No.: 478,347

[22] Filed: Jun. 7, 1995

[51] Int. Cl.$^6$ ............................................. A61K 31/70
[52] U.S. Cl. .................................. 514/54; 536/122
[58] Field of Search ............................. 536/122; 514/54

[56] References Cited

U.S. PATENT DOCUMENTS

| | | | |
|---|---|---|---|
| 4,820,693 | 4/1989 | Gillespie | 514/25 |
| 4,966,890 | 10/1990 | Gillespie | 514/25 |
| 5,032,679 | 7/1991 | Brandley et al. | |

OTHER PUBLICATIONS

Hasdai, et al., *Coronary Art. Dis.*, vol. 5, No. 1, pp. 81–91.
Peten, *J. Am. Soc. Neph.*, vol. 41, p. 780, 111p, Non–Anticoagulant Heparin Suppresses α11 Collagen mRNA and Reduces Laminin B1 Expression in Sclerotic Glomeruli from Mice Transgenic for Growth Hormone (GH Mice) (1993).
Kaizu, et al., *Jap. J. Neph.*, vol. 35, No. 1, pp. 35–42 (1993).
Floege, et al., *Kid. Int.*, vol. 43, pp. 369–380 (1993).
Striker, et al., *Diabetes/Metabolism Rev.*, vol. 9, No. 1, pp. 37–56 (1993).
Tan, et al., *Am. J. Path.*, vol. 142, No. 2, pp.463–470 (1993).
Kanabrocki, et al., *Quat. J. Med.*, New Series 83, No. 300, pp. 259–282 (1992).
Naparstek, et al., *Arth. & Rheum.*, vol. 33, No. 10, pp. 1554–1559 (1990).
Wardle, *J. Int. Med. Res.*, vol. 20, pp. 361–370 (1992).
Peten, et al., *J. Exp. Med.*, vol. 176, pp. 1571–1576 (1992).
Peten, et al., *Am. J. Physiol.*, vol. 263, pp. F951–F957 (1992).
Striker, et al., *Lab. Inv.*, vol. 64, No. 4., pp. 446–456 (1991).
Pesce, et al., *Lab. Inv.*, vol. 65, No. 5, pp. 601–605 (1991).
Nakamura, et al., *Lab. Inv.*, vol. 64, No. 5, pp. 640–647 (1991).
Tan, et al., *Biochem. J.*, vol. 278, pp. 863–869 (1991).
Wilke, et al., *Cleveland Clin. J. Med.*, pp. 753–754 (Nov./Dec. 1989).
Karnovsky, et al., *Ann. N.Y. Acad. Med.*, vol. 556, pp. 268–281 (1989).
Herbert, et al., *Path. Biol.*, vol. 37, No. 7, pp. 847–850 (1989).
Purkerson, et al., *J. Clin. Invest.*, vol. 81, pp. 69–74 (1988).
Herbert, et al., *Artery*, vol. 16, No. 1, pp. 1–14 (1988).
Adler, *Am. J. Physiol.*, vol. 255, pp. F781–F786 (1988).
Herbert, et al., *Biochem. Pharm.*, vol. 37, No. 22, pp. 4281–4288 (1988).
Slugeň, *Int. Urol. Neph.*, vol. 20, No. 3, pp. 313–314 (1988).
Ichikawa, et al., *Kid. Int.*, vol. 34, pp. 638–644 (1988).
Paul, et al., *Thrombosis Res.*, vol. 46, pp. 793–801 (1987).
Jacques, et al., *Artery*, vol. 14, No. 4, pp. 209–215 (1987).
Rosenberg, et al., *Ann. N.Y. Acad. Science*, vol. 454, pp. 270–278 (1985).
Delvos, et al., *Blut*, vol. 51, pp. 127–136 (1985).
Andrews, et al., *Chem. Bio. Interactions*, vol. 47, pp. 157–173 (1983).
Golding, et al., *Current Ther. Res.*, vol. 33, No. 2 (1983).
Berthoux, et al., *Path. Biol.*, vol. 25, pp. 33–36 (1977).
Fye, et al., *Arch. Intern. Med.*, vol. 136, pp. 995–999 (1976).
Bone, et al., *Kid. Int.*, vol. 8, pp. 72–79 (1975).
Zimmerman, et al., *Nephron*, vol. 12, pp. 219–230 (1974).
Suc, et al., *Pers. Neph. & Hyper.*, vol. 1, Pt. 2, pp. 927–947 (1973).
Arieff, et al., *Arch. Intern. Med.*, vol. 129, pp. 77–84 (1972).
Lindeman, *Klin. Mbl. Augenheilk*, vol. 161, pp. 100–103 (1972).
Freedman, et al., *Inv. Urol.*, vol. 7, No. 5, pp. 398–409 (1970).
Kincaid–Smith, et al., *The Lancet*, pp. 1360–1363 (1968).
SP$_{54}$ Package Insert for pentosanpolysulphate sodium, Bene Arzneimittel GmbH.

*Primary Examiner*—Elli Peselev
*Attorney, Agent, or Firm*—Kirschstein, et al.

[57] ABSTRACT

A method of treating a mammalian patient suffering from a chronic progressive vascular disease (CPVD) characterized by scarring and/or fibrosis to halt the progress of the disease and cause resolution of already-formed scarring or fibrotic lesions. The method consists of the administration to the patient of a pharmaceutical composition containing an effective amount of pentosan polysulfate (PPS) or a pharmaceutically acceptable salt thereof. The oral route of administration is preferred, with total daily dosage of PPS or PPS salt ranging from about 50 to 1200 mg per day.

14 Claims, 17 Drawing Sheets

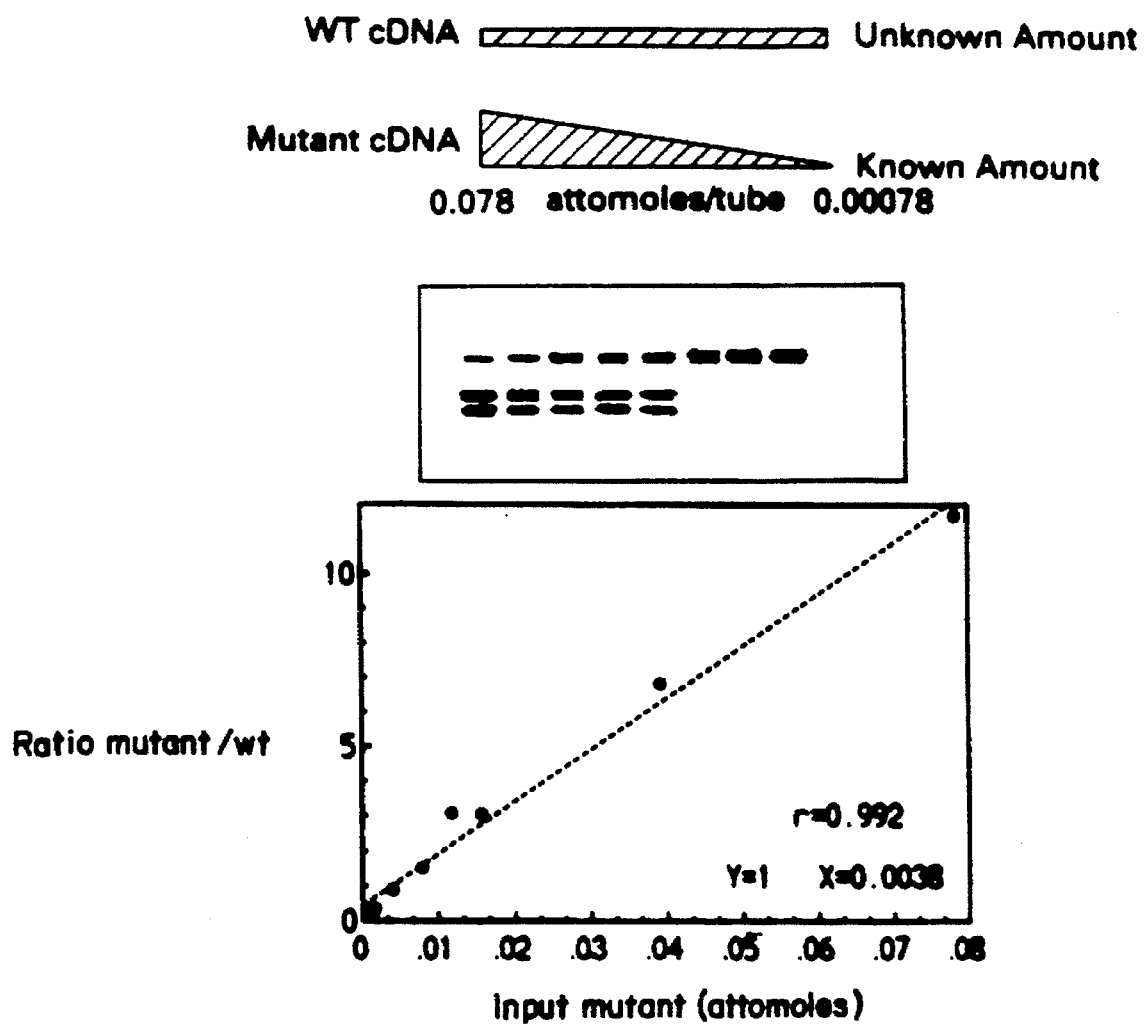

Effects of PPS on mRNA levels

| Day | αIIV | αII | 72KDa | 92KDa | TGF-b | β-actin |
|---|---|---|---|---|---|---|
| 1 | − | − | − | − | − | − |
| 3 | − | ↓ | − | ↑ | ↓ | − |
| 5 | − | ↓ | − | ↑ | ↓ | − |

Molecules

FIG. 9

FIG. 12 Oral PPS (Pentosan Polysulphate) Treatment in bGH Transgenic Mice (2 weeks, in drinking water)
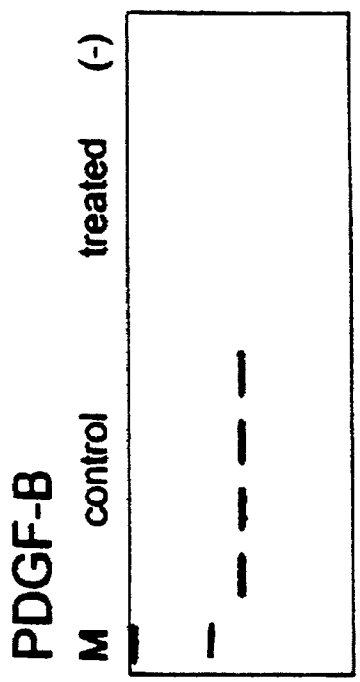
TGF-β1
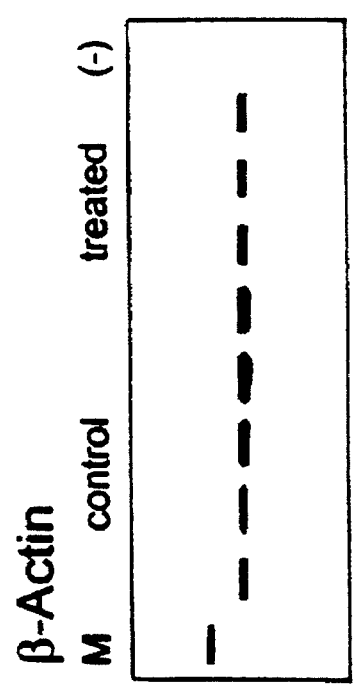
PDGF-B
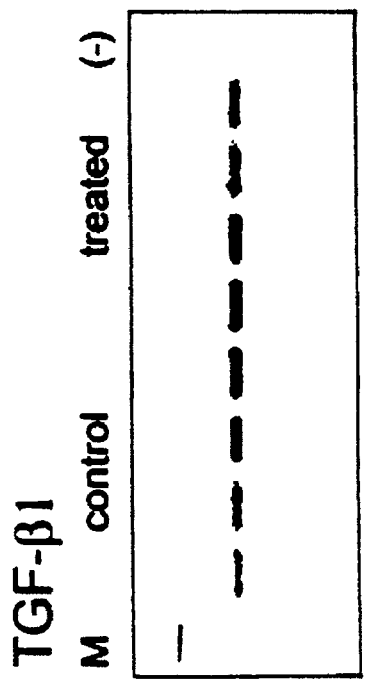
α-Smooth Muscle Actin
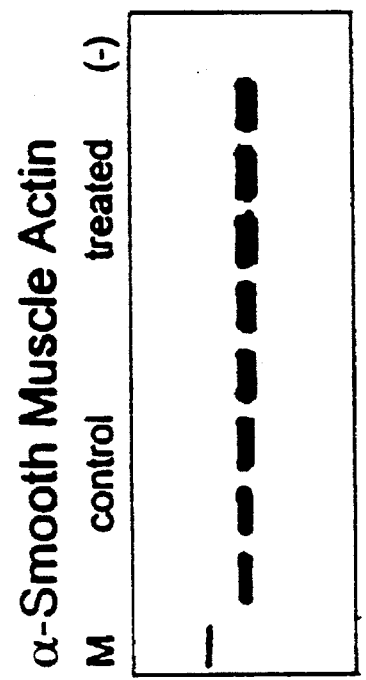
β-Actin

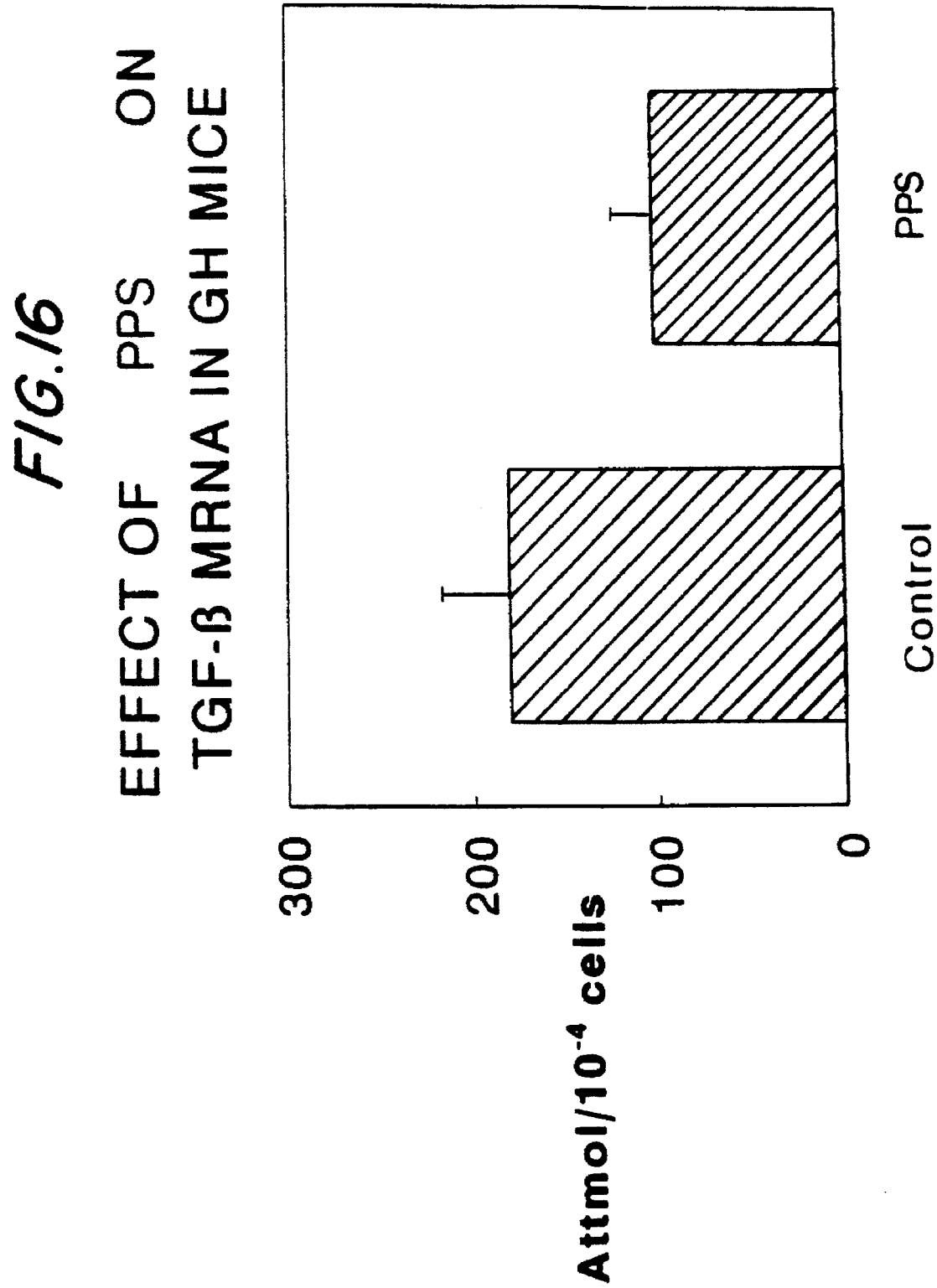
FIG. 16 EFFECT OF PPS ON TGF-β MRNA IN GH MICE

METHOD OF TREATING CHRONIC PROGRESSIVE VASCULAR DISEASES

BACKGROUND OF THE INVENTION

1. Field of the Invention

The invention relates to methods and pharmaceutical compositions used to treat chronic progressive vascular diseases.

2. Description of the Prior Art

Chronic progressive vascular disease (CPVD) is a complication of several of the most common diseases afflicting the developed world, including diabetes mellitus, hypertension, the various hyperlipidemias, and the like. The present therapeutic modalities dealing with CPVD are aimed at the underlying causes. Unfortunately, for the most part there are no known cures, or their control is very difficult to accomplish in the general population. In addition, CPVD is often not only well-established, but also far-advanced, by the time that the underlying cause(s) come to medical attention. Thus, one is left with attempting to treat secondary complications, of which CPVD is the most serious because it leads to renal failure, strokes, heart disease and blindness.

Generally, CPVD is characterized by a change in vascular smooth muscle cells. One of the major changes is an increase in the amount and alteration of the types of connective tissue that they synthesize. This results in scarring and marked changes in function. In blood vessels, this leads to loss of elasticity, resulting in vessels which do not distend and contract and which have thickened walls and narrowed lumens. The end result is reduced blood flow or complete blockage. Examples of vascular diseases characterized by these pathophysiological processes include chronic progressive glomerular disease, e.g., diabetic-induced glomerulosclerosis (scarring); progressive renal failure after renal transplantation; occlusion of shunts used to provide vascular access in patents with endstage renal disease being treated with hemodialysis; other chronic small blood vessel diseases (such as in some patients with hypertension); recurrence of stenosis in patients who have undergone coronary bypass surgery; and diabetic retinopathy.

The therapeutic goal of any treatment for CPVD must be to decrease the already-formed excess of extracellular matrix (scarring) in order to restore normal vessel patency and function. However, there is currently no direct method of interfering with abnormalities in smooth muscle tissue metabolism or to modulate connective tissue synthesis, despite their importance in chronic progressive disease. Progression of these diseases has been considered to be both inevitable and irreversible.

Heparin and some of its analogs have been found to inhibit smooth muscle proliferation (see, e.g., Castellot et al., *J. Cell. Biol.*, 102: 1979–1984, 1986). However, these findings have only been applied to the *prevention* of vascular diseases, generally through parenteral administration, but not to the treatment and reversal of established lesions. Since less than 50% of patients at risk develop CPVD and it is not possible to predict precisely who will develop these diseases, nor how rapidly they will progress, a preventative therapeutic strategy is impractical. Furthermore, daily injections are not acceptable to most patients for the delivery of other than life-saving medications (such as insulin). It is therefore particularly important that a treatment regimen be developed for CPVD, preferably involving oral administration of a pharmaceutical agent of low toxicity, which is effacious in treating and reversing CPVD by causing regression and degradation of established lesions.

Pentosan polysulfate (PPS) is a highly sulfated, semi-synthetic polysaccharide with a molecular weight ranging from about 1,500 to 6,000 Daltons, depending on the mode of isolation. PPS may be in the same general class as heparins and heparinoids, but there are a number of differences in chemical structure, methods of derivation and physico-chemical properties between PPS and heparin. While heparin is usually isolated from mammalian tissues such as beef and pork muscles, liver and intestines, PPS is a semi-synthetic compound whose polysaccharide backbone, xylan, is extracted from the bark of the beech tree or other plant sources and then treated with sulfating agents such as chlorosulfonic acid or sulfuryl trichloride and acid. After sulfation, PPS is usually treated with sodium hydroxide to yield the sodium salt.

As illustrated by the following formulas,

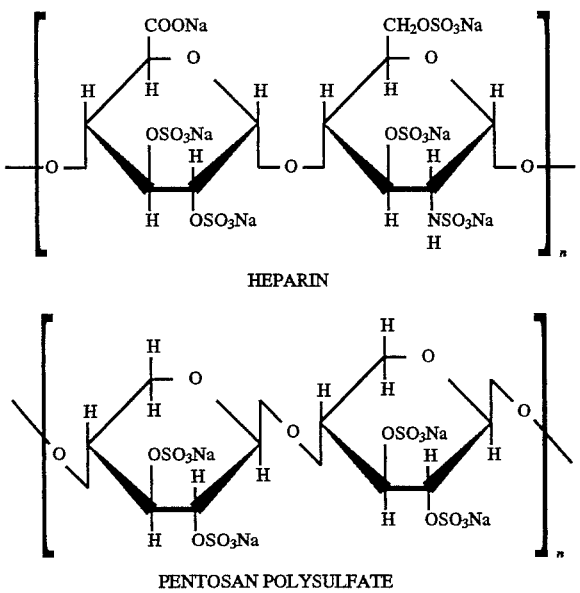

heparin is a sulfated polymer of repeating double sugar monomers, (D)-glucosamine and (D)-glucuronic acid (both 6-carbon hexose sugars), with an amine function on the glucosamine; PPS is a sulfated linear polymer of repeating single monomers of(D)-xylose, a 5-carbon pentose sugar in its pyranose ring form. While heparin rotates plane polarized light in a dextrorotatory direction, PPS rotates light in a levorotatory direction.

In terms of biological properties, PPS prolongs partial thromboplastin time and has been used to prevent deep venous thrombosis, but it has only about one-fifteenth the anticoagulant potency of heparin (see generally Wardle, *J. Int. Med. Res.*, 20:361–370, 1992). PPS has also been disclosed as useful in the treatment of urinary tract infections and interstitial cystitis (U.S. Pat. No. 5,180,715) and, in combination with an angiostatic steroid, in arresting angiogenesis and capillary, cell or membrane leakage (U.S. Pat. No. 4,820,693).

Some researchers have demonstrated that PPS inhibits smooth muscle cell proliferation and decreases hyperlipidemia, and on that basis have suggested that PPS might be useful prophylactically in limiting atherosclerotic plaque formation, inhibiting mesangial cell proliferation and preventing collagen formation and glomerulosclerosis (Paul et al., *Thromb. Res.*, 46:793–801, 1987; Wardle, ibid.). However, no one had previously considered that it was feasible to reverse vascular scarring, i.e., PPS had not been considered in this context.

SUMMARY OF THE INVENTION

1. Objects of the Invention

It is the object of the present invention to provide a method of treating CPVD not only to halt the disease process but to actually reverse that process and cause the regression of existing scarring or lesions. It is a further object of the invention to provide such a method of treatment utilizing a commercially available pharmaceutical agent which may be administered by conventional means, which is non-toxic and not likely to provoke serious side effects and which is highly efficacious in treating CPVD.

2. Brief Description of the Invention

In keeping with these objects and others which will become apparent hereinafter, the invention resides, briefly stated, in a method of treating a mammalian patient suffering from CPVD to halt the progress of the disease and to cause the resolution of already-formed scarring or fibrotic lesions in the affected organ or vasculature said method consisting of the administration to the patient of a pharmaceutical composition containing an effective vascular disease treatment amount of pentosan polysulfate or a pharmaceutically acceptable salt thereof. Oral administration of PPS, e.g., in the form of tablets, capsules or liquids, is the preferred mode of administration.

BRIEF DESCRIPTION OF THE DRAWINGS

FIG. 1 reflects the quantitation of $\alpha_1$IV collagen mRNA by competitive PCR on one-tenth of a glomerulus from a normal five-week old mouse (as described in Example 1 below), depicting:

a) in its top panel, the reaction scheme and a corresponding ethidium bromide stained gel after PCR amplification; and b) in its lower panel, a graph plotting the ratio of mutant collagen cDNA per glomerulus against the amount of mutant cDNA inputted into each of nine tubes containing all of the PCR reagents.

FIG. 2 depicts:

a) in its upper panel, PAS-stained kidney sections from two nephrectomy specimens with renal carcinoma (A-normal glomerular histology; B-marked sclerosis);

b) in its middle panel (C-D), immuno-fluorescence microscopy, antibody to type IV collagen in the same kidneys; and c) in its lower panel (E), a bar graph reflecting the sclerosis index in the same kidneys; $\alpha_2$IV collagen cDNA was determined by competitive PCR quantitation of in pools of 50 microdissected glomeruli (values are: 145 ±22 vs. 1046 ±74 ×$10^{-4}$ attomoles/glomerulus.

Figure 2A:
Figure 2B:
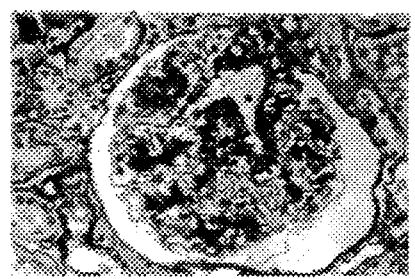
Figure 2C:
Figure 2D:
Figure 2E:
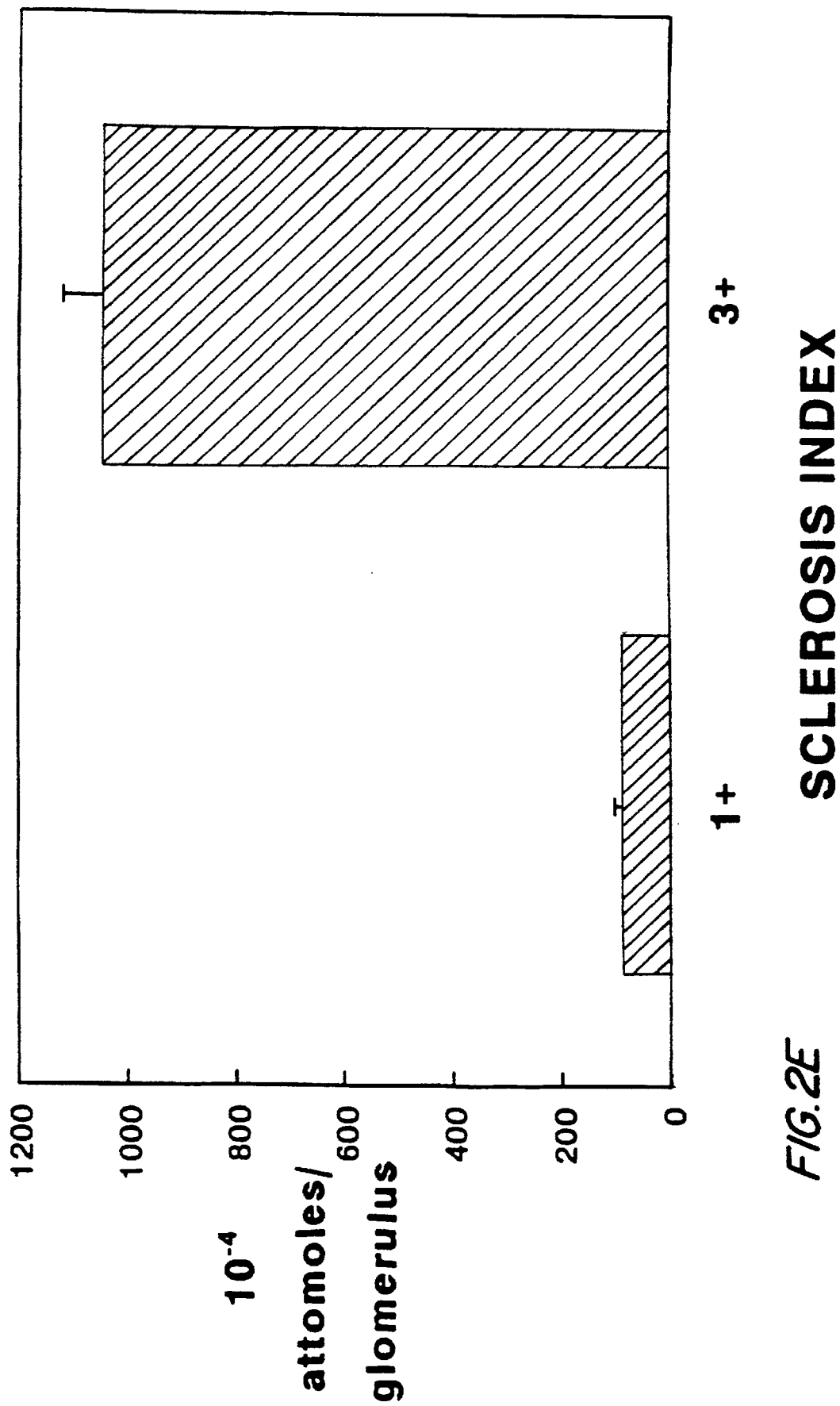
Figure 3:
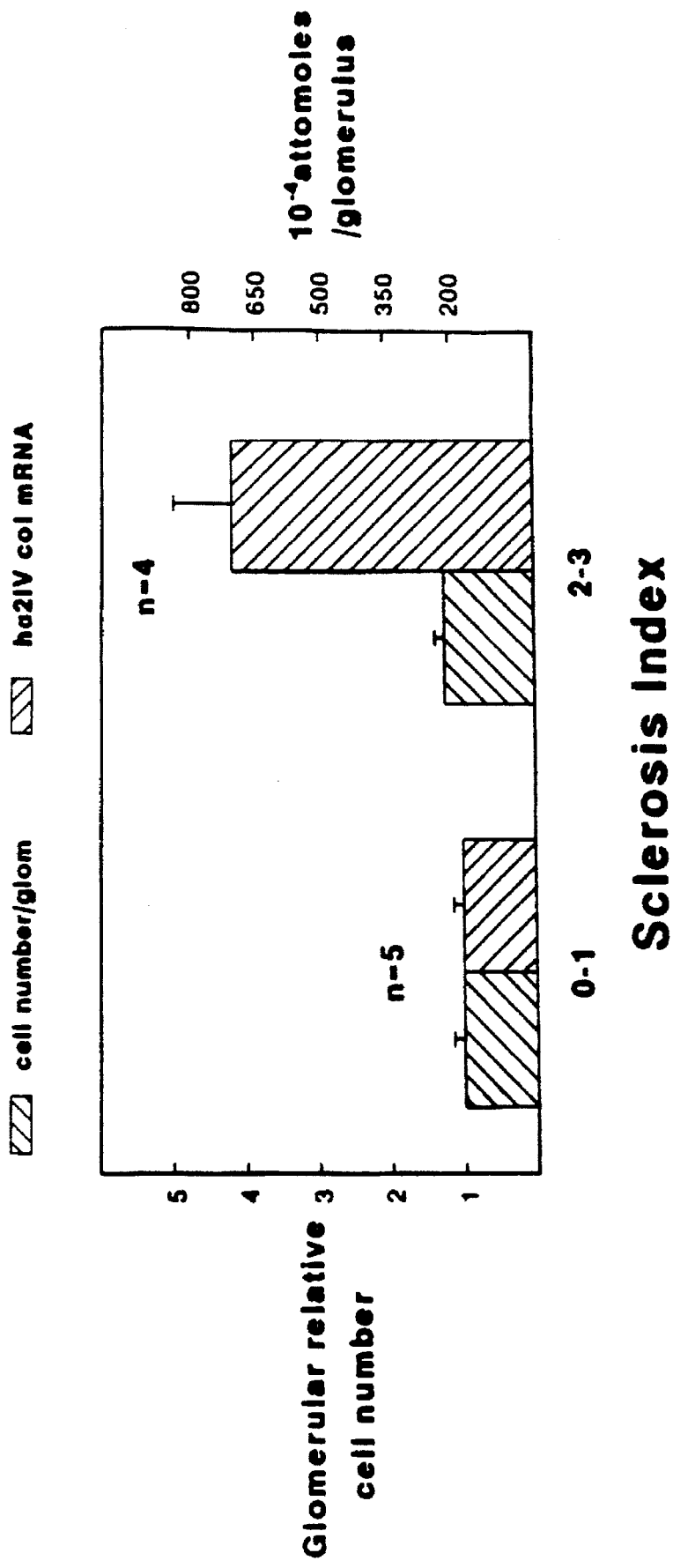

FIG. 3 is a bar graph reflecting the sclerosis index in the kidneys of five human patients without glomerular sclerosis compared to five patients with sclerosis, expressed in glomerular relative cell numbers and $\alpha_2$IV collagen cDNA levels.

Figure 4:
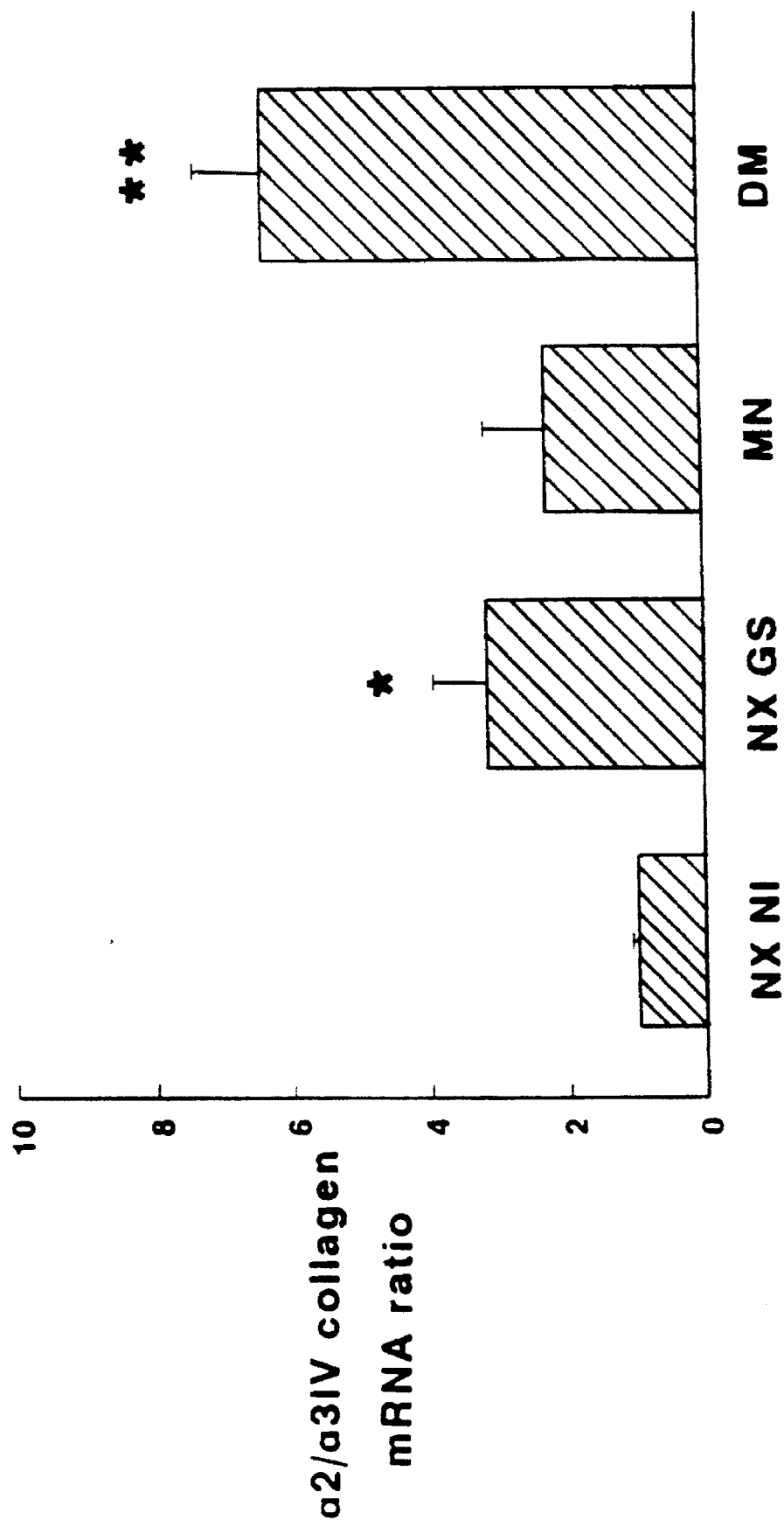

FIG. 4 is a bar graph reflecting $\alpha_2/\alpha_3$IV collagen mRNA ratios from human patients with membranous glomerulonephritis (MN) and diabetic nephropathy (DM) and from nephrectomies with glomerulosclerosis (NX GS) and without glomerulosclerosis (NX N1.

Figure 5:
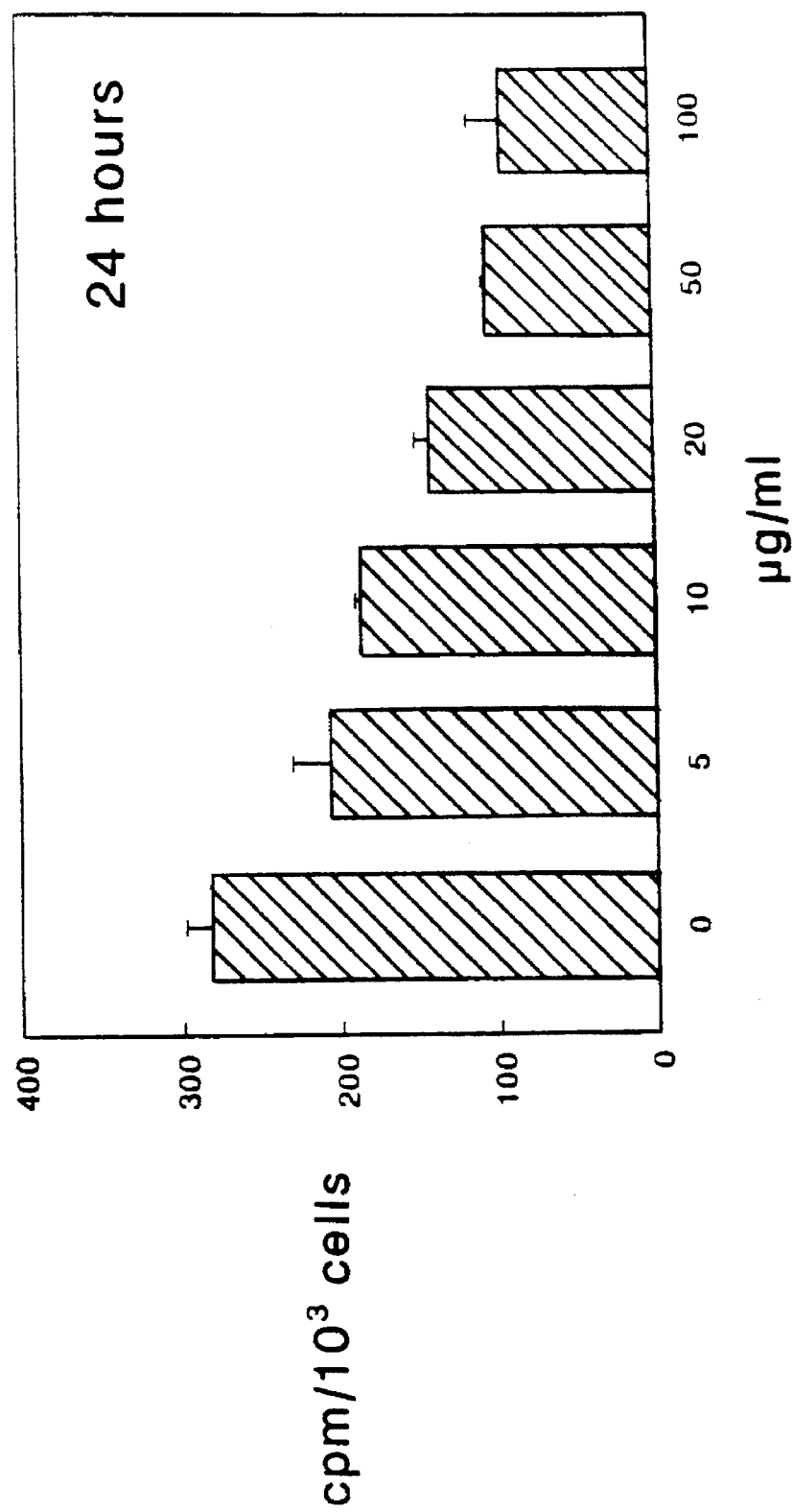

FIG. 5 is a bar graph reflecting the effect of PPS on DNA synthesis in normal mesangial cells as determined by tritiated thymidine incorporation (24 hours of incubation) and plotted as tritiated counts per minute per $10^3$ cells vs. concentration of PPS in µg/ml.

Figure 6:
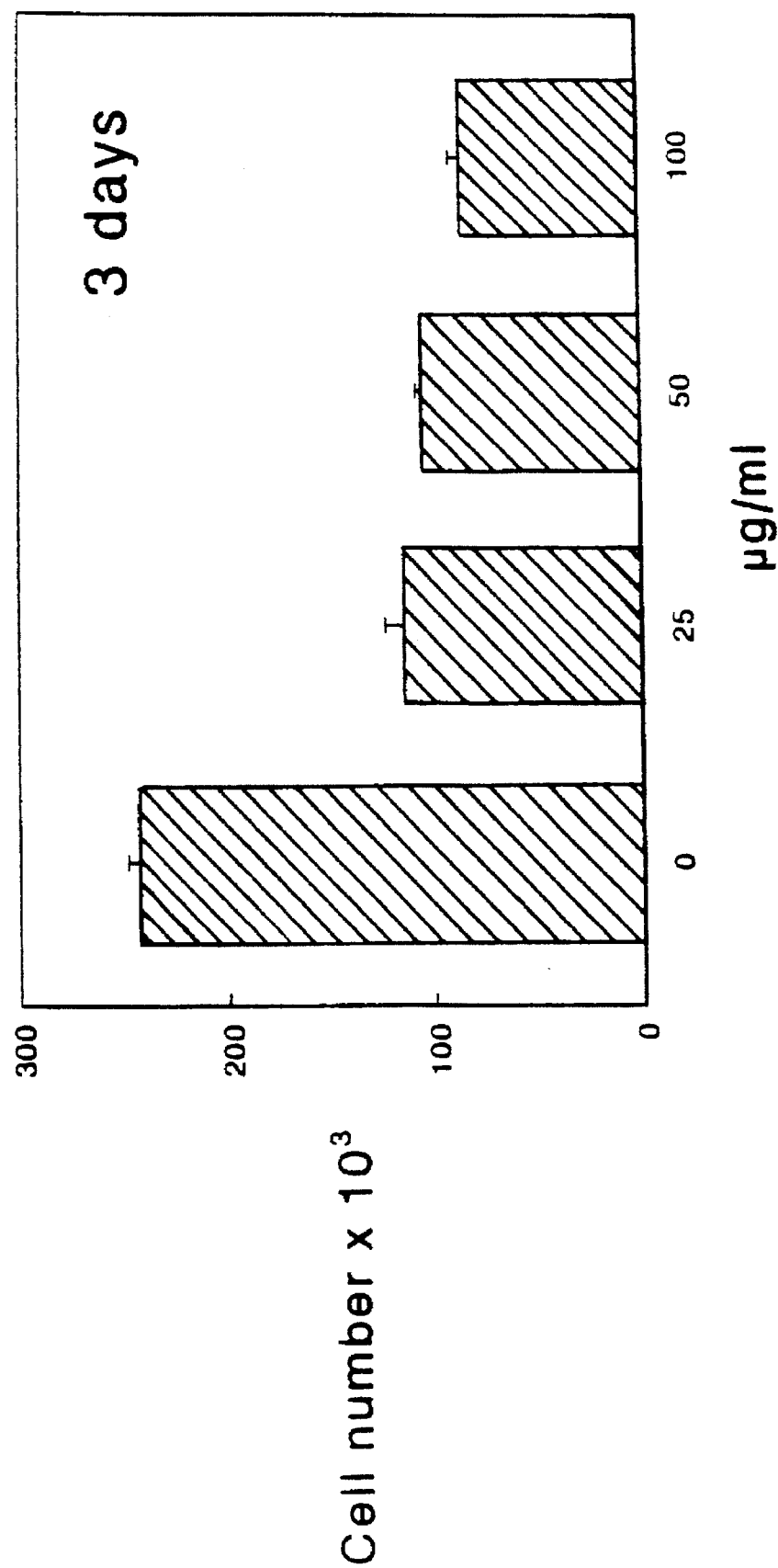

FIG. 6 is a bar graph reflecting the effect of PPS on cell growth in normal mesangial cells plotting cell number after three days of incubation vs. added concentration of PPS in µg/ml.

Figure 7:
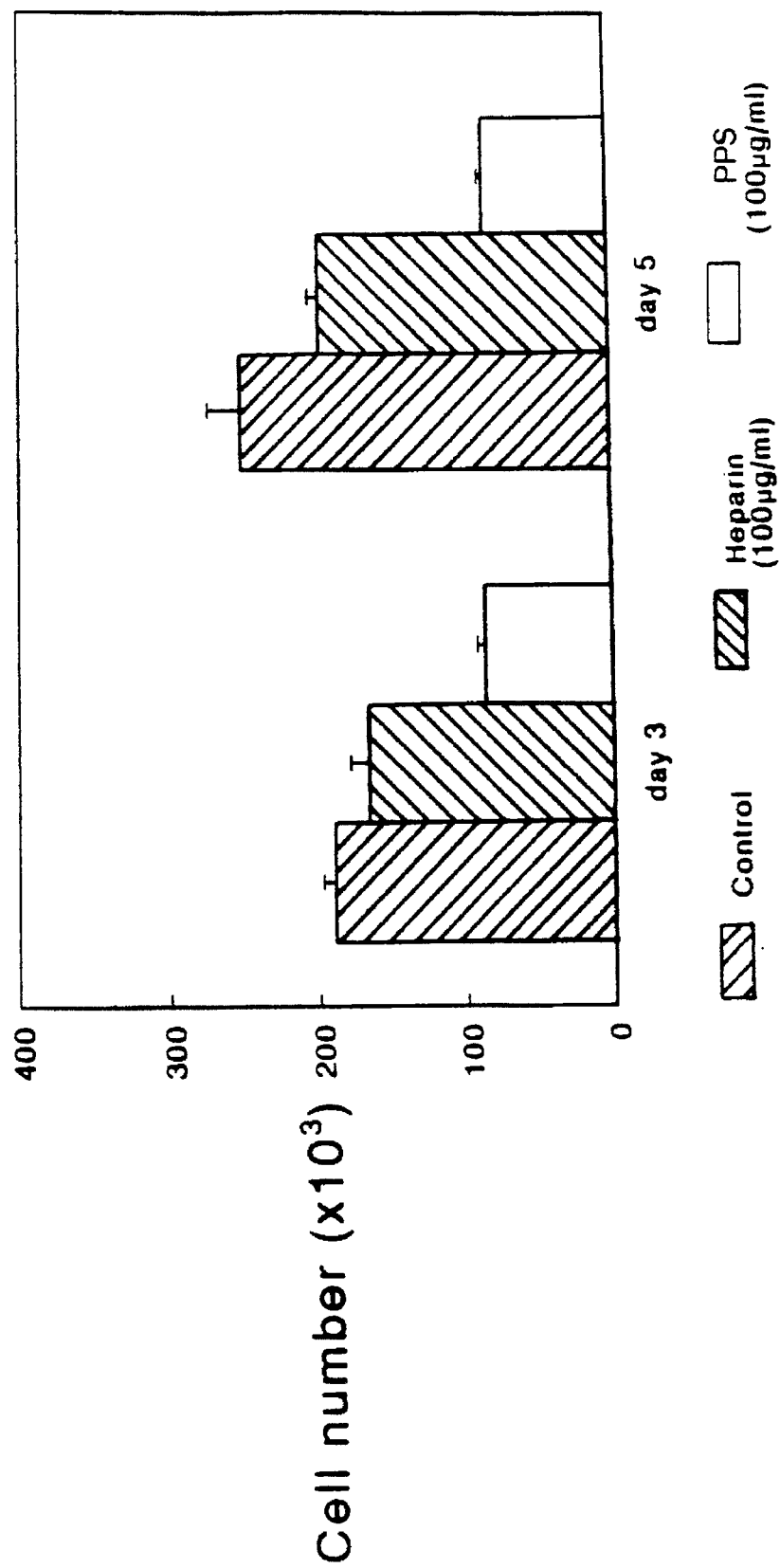

FIG. 7 is a bar graph reflecting a comparison of the effects of PPS and heparin (with an untreated control group) on cell growth in normal mesangial cells after three and five days of incubation.

Figure 8:
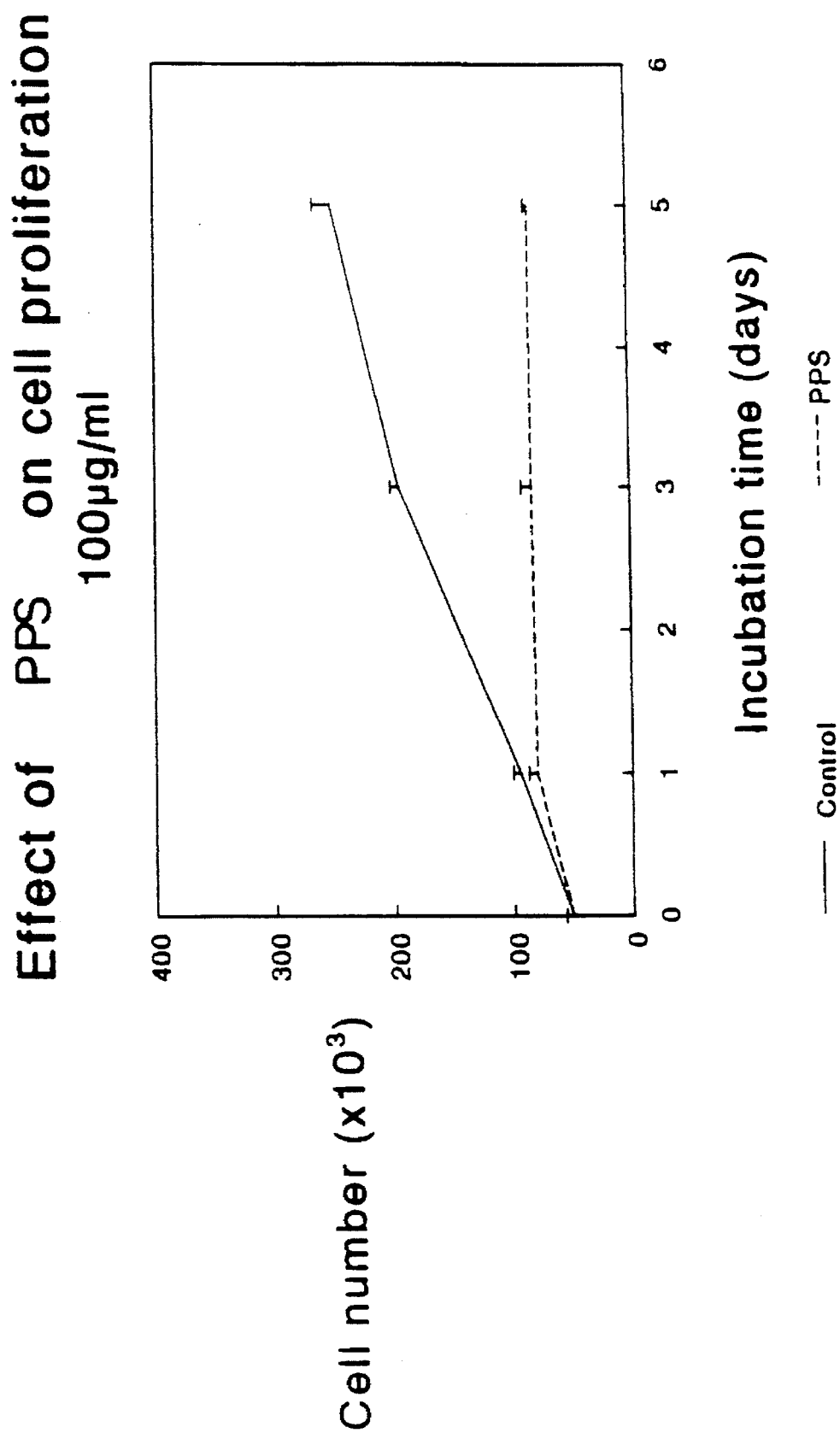

FIG. 8 is a graph reflecting normal mesangial cell proliferation over time in cells incubated with serum and PPS compared to control cells incubated only with serum.

FIG. 9 is a chart of mRNA values from normal mesangial cell layers exposed to PPS (100 µg/ml) for varying periods and reverse-transcribed, reflecting the increase, decrease or lack of change in levels of $\alpha_1$ IV and $\alpha_1$ I collagen mRNA, collagenases (metalloproteinases) 72 KDa and 92 KDa mRNA, growth factor TGF-$\beta$ mRNA and cell protein $\beta$-actin mRNA.

Figure 10:
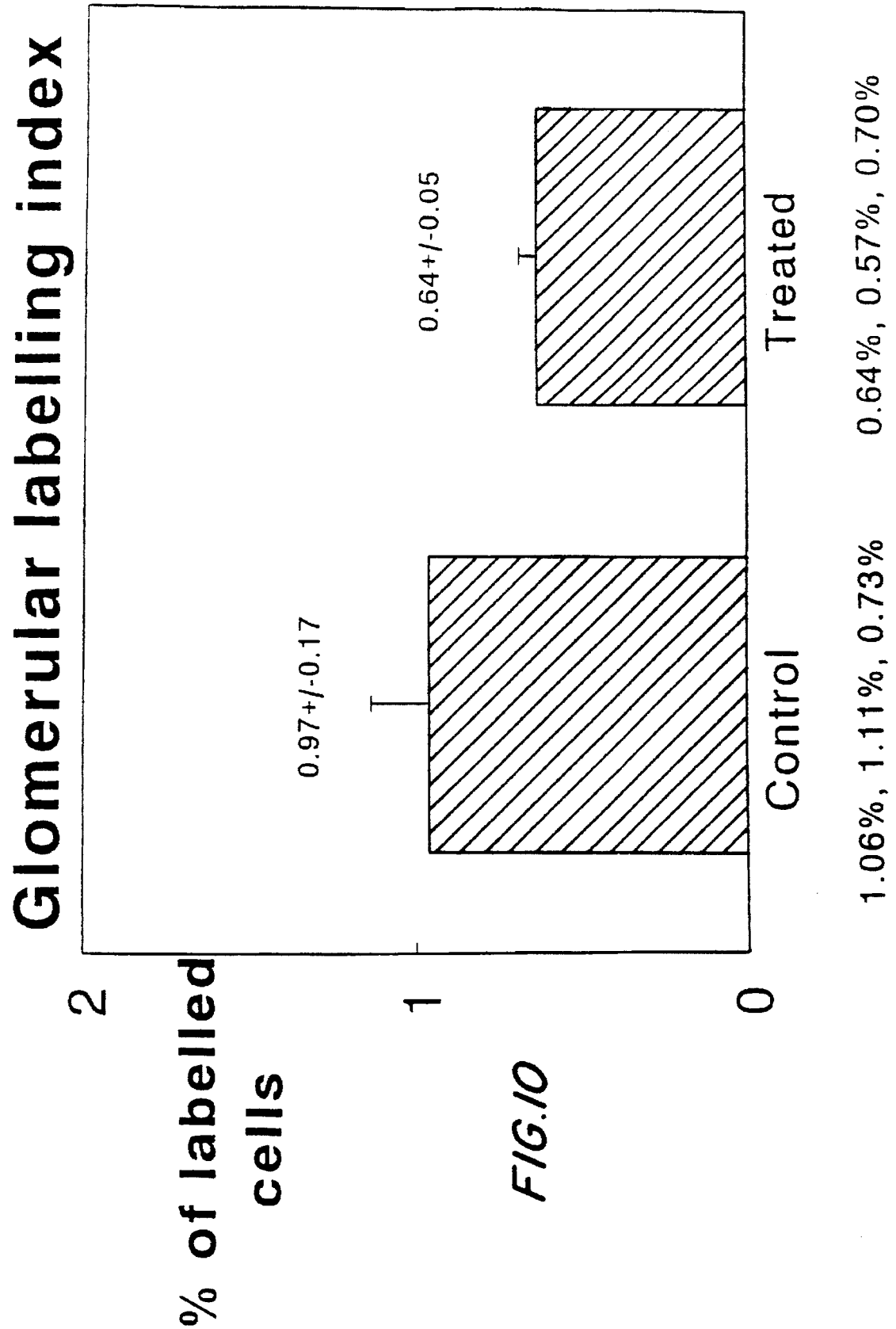

FIG. 10 is a bar graph reflecting the glomerular labeling index (by percentage of labeled cells) in glomeruli of kidneys of GH transgenic mice administered PPS in drinking water compared with glomeruli from control mice receiving untreated water.

Figure 11:
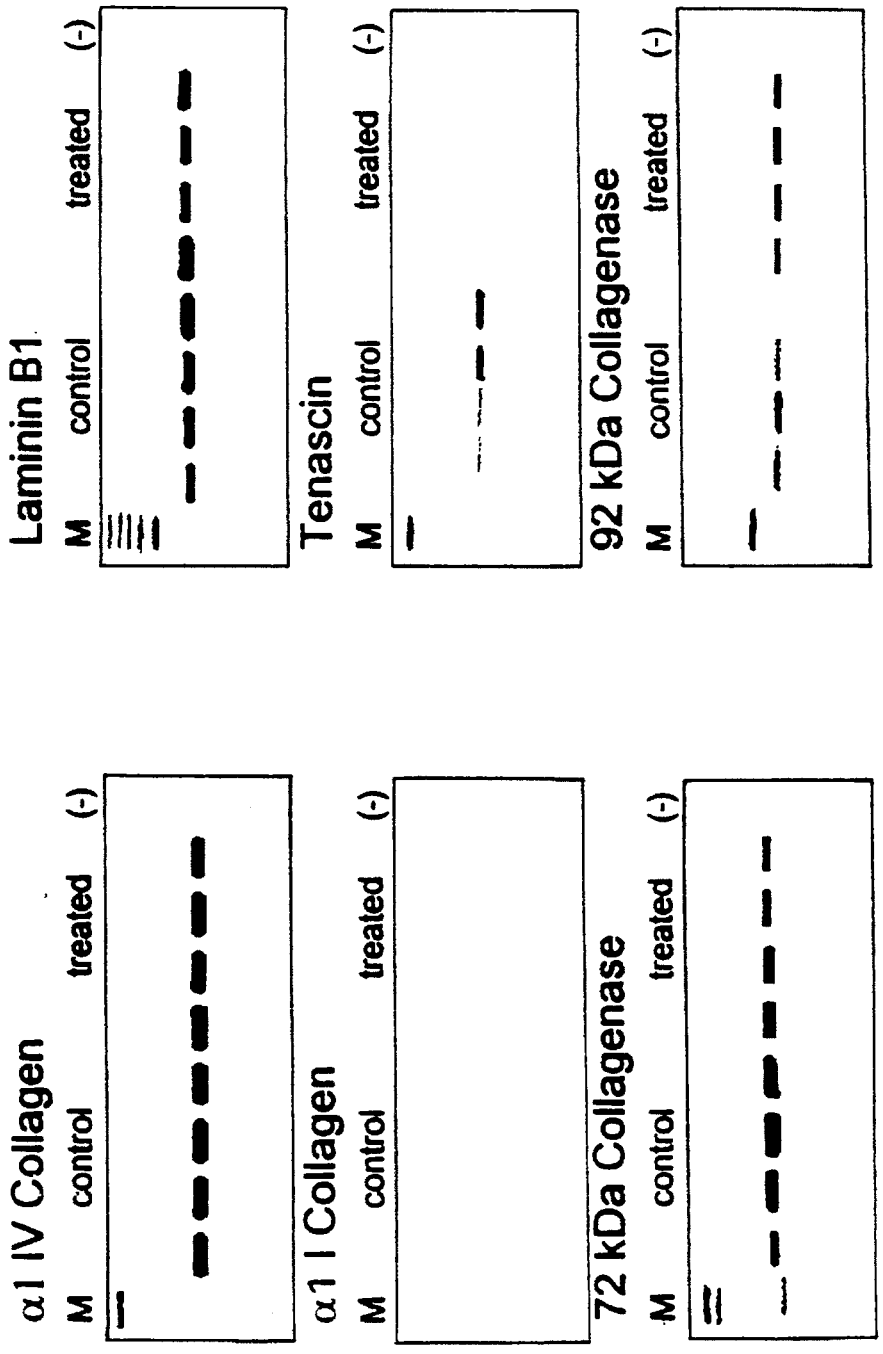

FIG. 11 depicts the results of competitive PCR assays with various collagen types, collagenases and basement membrane glycoproteins in the glomeruli of PPS-treated GH transgenic mice as analyzed using a laser densitometer.

FIG. 12 depicts the results of competitive PCR assays with various growth factors and actin proteins in the glomeruli of PPS-treated GH transgenic mice as analyzed using a laser densitometer.

Figure 13:
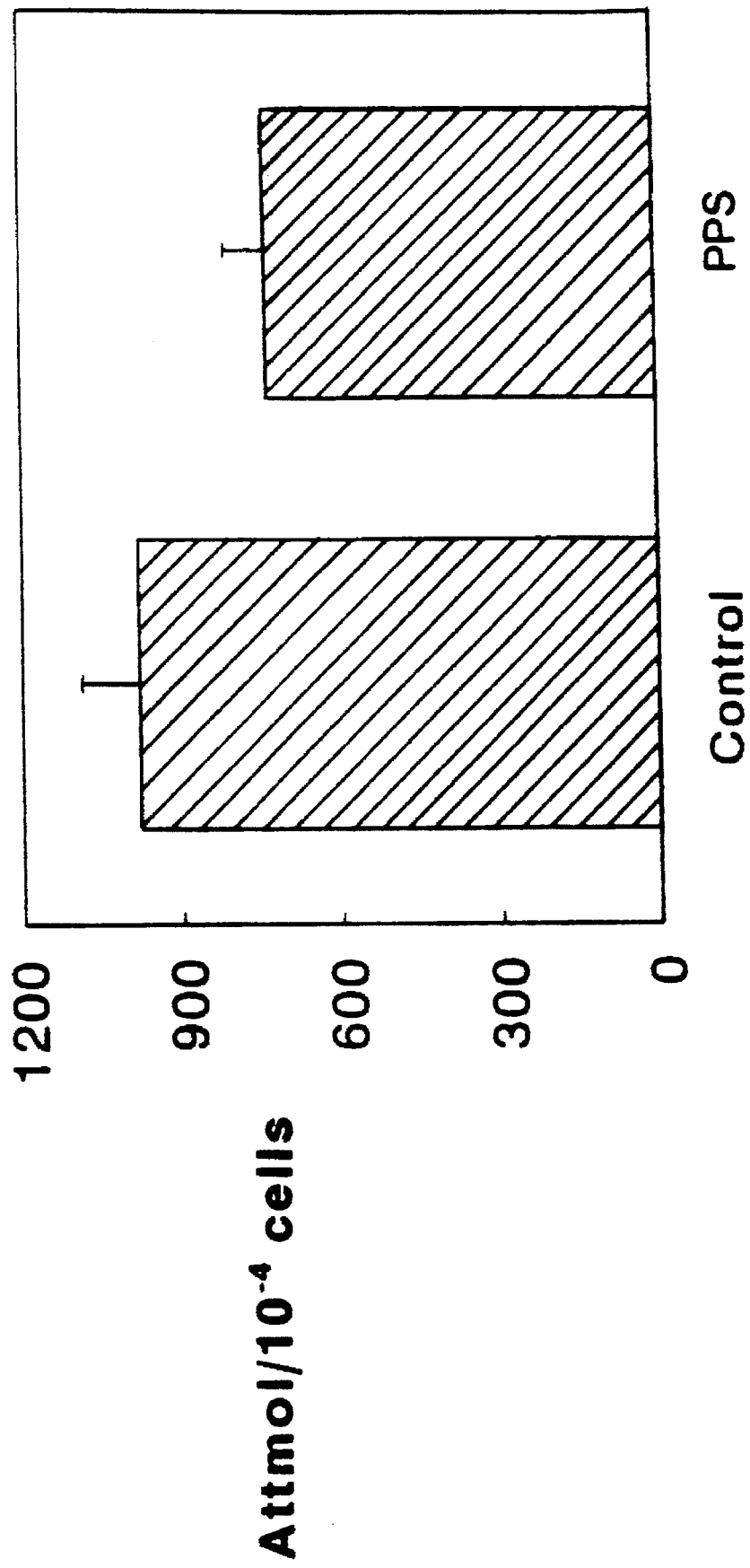

FIG. 13 is a bar graph reflecting a comparison of the relative amounts of $\alpha_1$IV collagen mRNA elaborated by the glomeruli of GH transgenic mice administered PPS in drinking water with a control group of untreated mice.

Figure 14:
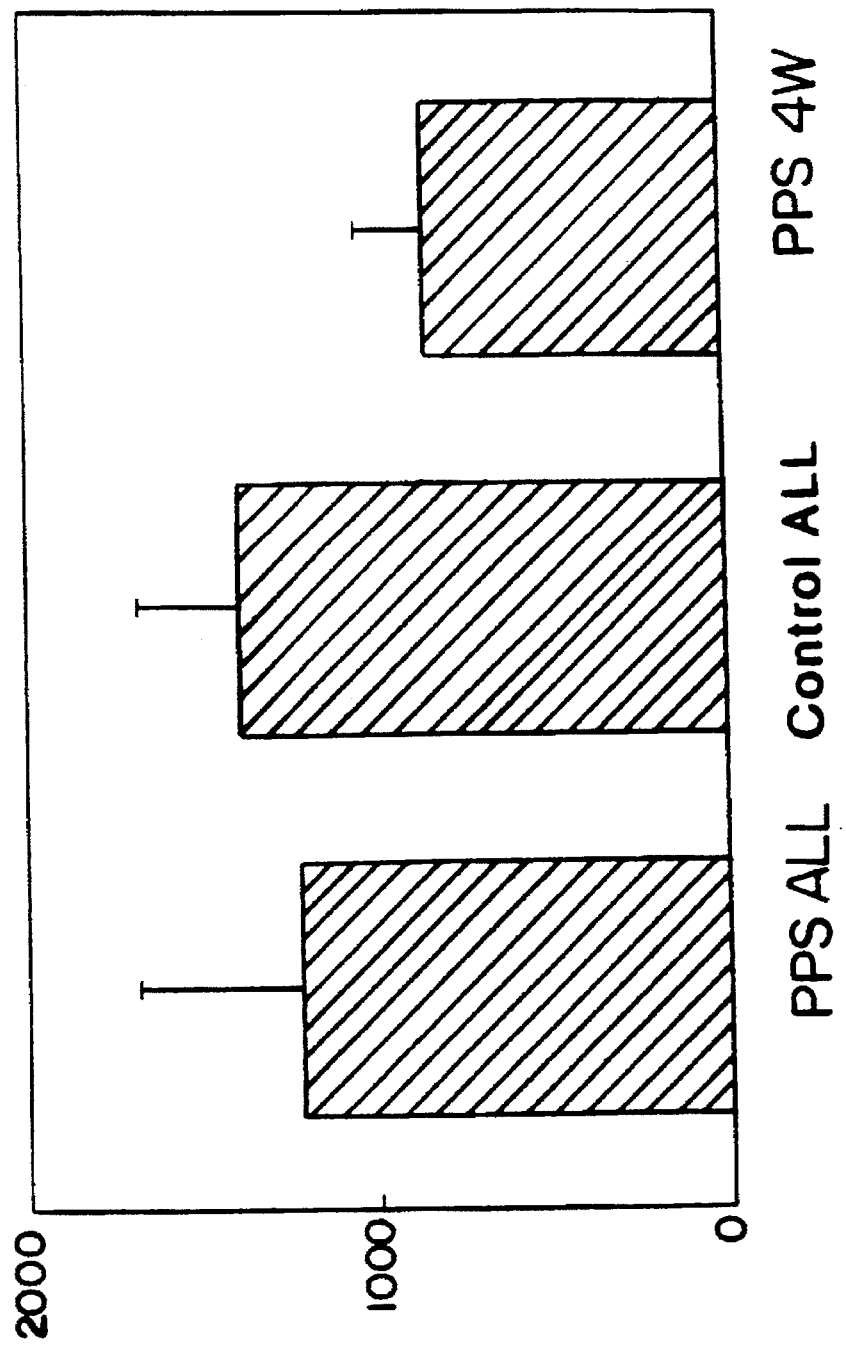

FIG. 14 is a bar graph reflecting a comparison of the relative amounts of laminin $B_1$ mRNA elaborated by the glomeruli of (a) four GH transgenic mice administered PPS in drinking water (2 for 2 weeks and 2 for 4 weeks), (b) a control group of untreated mice and (c) the two mice treated with PPS for 4 weeks.

Figure 15:
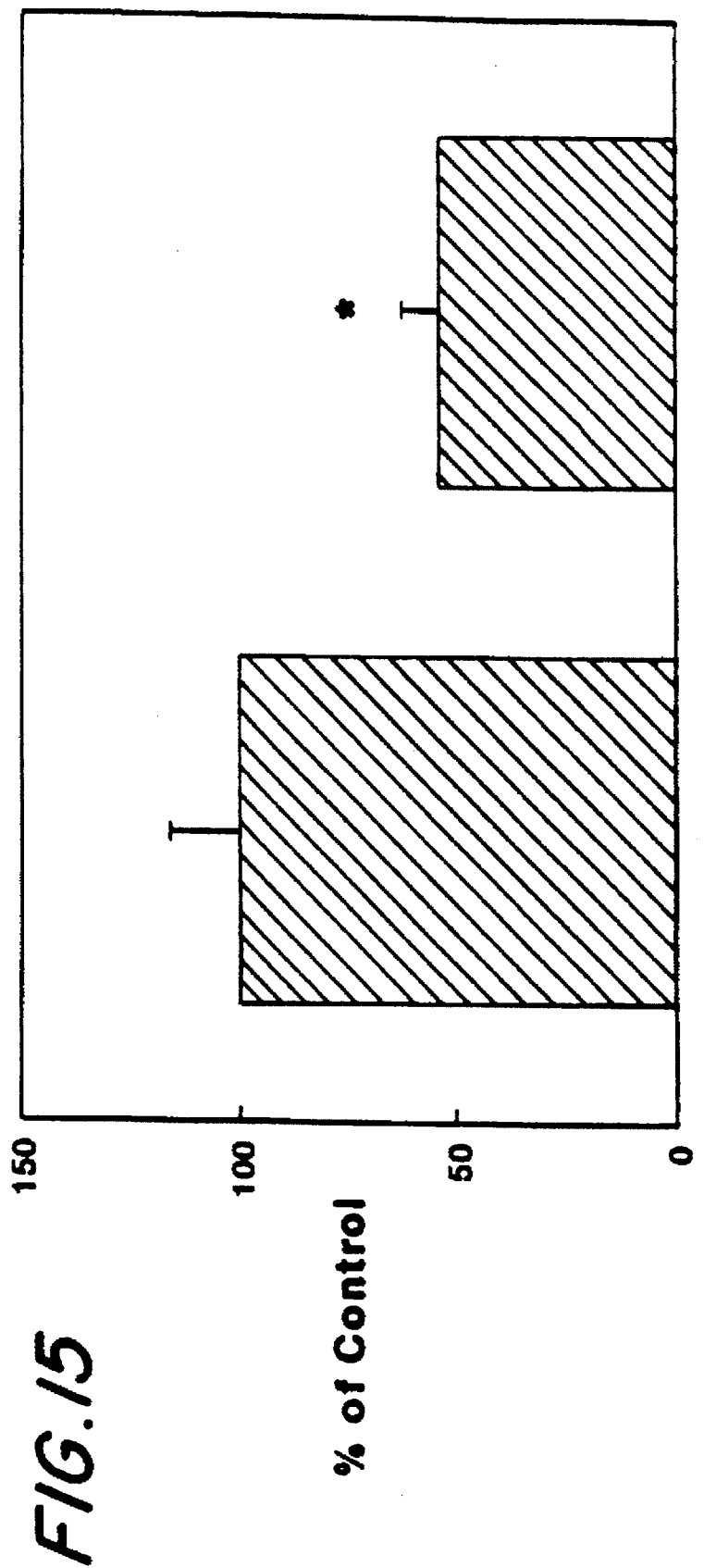

FIG. 15 is a bar graph reflecting a comparison of the relative amounts of platelet-derived growth factor PDGF-B mRNA elaborated by the glomeruli of GH transgenic mice administered PPS in drinking water with a group of untreated mice.

FIG. 16 is a bar graph reflecting a comparison of the relative amounts of growth factor TGF-$\beta$ mRNA elaborated by the glomeruli of GH transgenic mice administered PPS in drinking water with a group of untreated mice.

DETAILED DESCRIPTION OF THE INVENTION

The present invention relates to a method of treating a mammalian patient suffering from a chronic progressive vascular disease (CPVD) characterized by scarring and/or fibrosis in the affected organ or vasculature to halt the progress of the disease and cause the dissolution or resolution of already-formed scarring or fibrotic lesions. The subject method consists of the administration to the patient of a pharmaceutical composition containing an effective vascular disease treatment amount of pentosan polysulfate (PPS) or a pharmaceutically acceptable salt thereof.

The diseases which may be treated in accordance with the novel method include, but are not limited to, chronic progressive glomerular disease, including diabetic-induced glomerulosclerosis (scarring); progressive renal failure after renal transplantation; occlusion of shunts used to provide vascular access in patents with endstage renal disease being treated with hemodialysis; other chronic small blood vessel diseases (such as in some patients with hypertension);

recurrence of stenosis in patients who have undergone coronary bypass surgery; and diabetic retinopathy.

The phrase "an effective vascular disease treatment amount" as used herein refers to an amount of PPS or salt thereof incorporated into a pharmaceutical composition which is effective when given one or more times daily for a prescribed period of time in halting and reversing the progressive symptoms of scarring-type CPVD. In human patients, a total daily dosage of about 50 to about 1200 mg, and preferably from about 100 to about 600 mg, of PPS administered in one to four equally divided doses is effective in achieving the therapeutic goal of treating and reversing CPVD. In smaller mammals, the dosage range may have to be adjusted downward in accordance with body weight, species and the nature of the condition. The invention is not limited, however, to any specific daily dosage range of PPS, but instead broadly encompasses the administration of PPS as an active pharmaceutical agent to treat CPVD in mammals.

The preferred embodiment of the novel method of treatment is the administration to the patient of a pharmaceutical composition comprising an effective amount of PPS and at least one pharmaceutically acceptable inert ingredient. The composition may be in any standard pharmaceutical dosage form, but is preferably an orally administered dosage form.

Dosage forms for oral delivery may include conventional tablets, coated tablets, capsules or caplets, sustained release tablets, capsules or caplets, lozenges, liquids, elixirs or any other oral dosage form known in the pharmaceutical arts.

As pharmaceutically acceptable inert ingredients there are contemplated fillers, binders, solvents, etc. which do not interfere with the CPVD treatment activity of the PPS. Also, fillers such as clays or siliceous earth may be utilized if desired to adjust the size of the dosage form. Further ingredients such as excipients and carriers may be necessary to impart the desired physical properties of the dosage form. Such physical properties are, for example, release rate, texture and size. Examples of excipients and carriers useful in oral dosage forms are waxes such as beeswax, castor wax, glycowax and carnauba wax, cellulose compounds such as methylcellulose, ethylcellulose, carboxymethylcellulose, cellulose acetate phthalate, hydroxypropylcellulose and hydroxypropylmethyl-cellulose, polyvinyl chloride, polyvinyl pyrrolidone, stearyl alcohol, glycerin monstearate, methacrylate compounds such as polymethacrylate, methyl methacrylate and ethylene glycol dimethacrylate, polyethylene glycol and hydrophilic gums.

In the compositions of the present invention the PPS active ingredient is desirably present in an amount between about 50 and about 300 mg per dosage unit. The exact dosage administered to each patient will be a function of the condition being treated and the physical characteristics of the patient, such as age and body weight.

The active pharmaceutical ingredient can be PPS or a pharmaceutically acceptable salt thereof, e.g., the sodium salt. One preferred oral dosage form for use in the method of the invention is Elmiron® gelatin capsules (Baker Norton Pharmaceuticals, Inc., Miami, Fla.) which contain 100 mg of PPS sodium and, as excipients, microcrystalline cellulose and magnesium stearate.

Although the oral route of administration is preferred, the present method of treatment also comprehends the administration of PPS or a salt thereof via the parenteral, transdermal, transmucosal routes or via any other routes of administration known and conventionally utilized in the medical and pharmaceutical arts. Likewise, the compositions of the invention may include PPS in pharmaceutically acceptable parenteral, transdermal, transmucosal or other conventional vehicles and dosage forms together with suitable inert solvents, excipients and additives. Many examples of such pharmaceutically acceptable vehicles can be found in Remington's Pharmaceutical Sciences(17th edition (1985)) and other standard texts. Whatever route of administration or type of pharmaceutical dosage form is used, the dosage range for the PPS active ingredient is from about 50 to about 1200 mg/day, and preferably about 100 to about 600 mg/day, although dosage amounts towards the lower end of that range would probably be utilized on parenteral administration.

The pharmaceutical compositions used in the method of the invention may include active ingredients other than PPS or a PPS salt, for example, other agents which may be useful in the management of CPVD.

The novel method enables convenient, safe and effective treatment of patients suffering from various forms of CPVD which in many instances may be life or organ threatening. By the subject method a pharmaceutical agent proven to have low toxicity and a low incidence of side effects can be used to not only halt what has long been considered the inexorable progress of chronic vascular disease, but actually degrade already-formed scarring and lesions to restore normal vessel patency and function.

The following examples include (a) descriptions of experiments already published in the medical literature which validate the use of certain competitive PCR (polymerase chain reaction) techniques for the quantitation of scarring-type collagen mRNA and related factors in glomeruli, and which demonstrate that relative glomerular cell numbers do not correlate with levels of production of scarring-type collagen, and (b) experiments conducted by or under the supervision of the inventors which demonstrate in vitro and in vivo the efficacy of PPS in down-regulating the production of scarring-type collagen and cell growth factors and up-regulating collagenese activity to degrade existing deposits of scarring collagen. These examples are not intended, however, to set forth materials, techniques or dosage ranges which must be utilized in order to practice the present invention, or to limit the invention in any way.

EXAMPLE 1

Quantitation of Collagen

As described in Peten et al., Am. J. Physiol., 32: F951–957 (1992), $\alpha_1 IV$ and $\alpha_2 IV$ collagen in mouse glomeruli can be quantitated by the following method: the amount of cDNA representing the mRNA in one-tenth of a glomerulus from a normal five-week old mouse and a standard amount of $\alpha_1 IV$ or $\alpha_2 IV$ collagen primers were added to each of several tubes containing all PCR reagents from the GeneAmp DNA Amplification Kit (Perkin-Elmer Cetus, Norwalk, Conn.). Serial dilutions of mutated cDNA containing either a new restriction enzyme cleavage site or a deletion were added to this mixture prior to amplification (scheme shown in FIG. 1, top panel). The concentrations of the mutant were determined in a prior experiment designed to bracket the equivalence point (y=1).

After PCR amplification, the entire reaction mix was loaded directly onto a 4% NuSieve:Seakem (3:1) (FMC Bioproducts, Rockland, Me.) agarose gel in a H5 Horizon gel apparatus (Life Technologies) and subjected to electrophoresis. DNA bands were visualized with ethidium bromide staining and ultraviolet (UV) transillumination. Photographs were taken with positive/negative 55 Polaroid films (Polaroid, Cambridge, Mass.) (see FIG. 1, middle panel). Gel negatives were scanned by one-dimensional laser densitometry, for competitive PCR analyses (Shimadzu; Scientific Instruments, Columbia, Md.).

The densitometric values of the test and the mutant band(s) were calculated, and their ratio for each reaction tube was plotted as a function of the amount of mutant template added (FIG. 1, bottom panel). For the $\alpha_2$IV collagen mutant, the measured densitometric band intensity was corrected by a factor of 562/479 before plotting the mutant/test band ratio. For the $\alpha_1$IV mutant bands, their densitometric values were added before division by the wild-type (test) band value. A straight line was drawn by linear regression analysis. The quantity of cDNA in the test sample was calculated to be that amount at which the mutant/test band density ratio was equal to 1. Competitive PCR assays were performed in duplicate or triplicate.

EXAMPLE 2

Changes in Sclerotic Glomeruli

As described in Peten et al., *J. Exp. Med.*, 176:1571–1576 (1992), unilateral nephrectomy specimens with renal carcinoma were obtained from human patients. The patients had no history of diabetes, hypertension or other systemic diseases associated with glomerular disease. Samples of cortical tissue distant from obvious tumor were placed in Carnoy's fixative, embedded in methacrylate or paraffin, and sections were stained with periodic acid-Schiff (PAS). The presence of glomerulosclerosis, defined as an expansion of the mesangial matrix, was independently evaluated by histological examination of PAS-stained material (FIG. 2, top panel) and by immunofluorescence microscopy of frozen sections after exposure to an antibody to type IV collagen (PHM-12, Silenus, Westbury, N.Y.) (FIG. 2, middle panel).

The competitive PCR assay was conducted as described in Example 1 to quantify the amount of $\alpha_2$IV (scarring-type) extracellular matrix collagen. The relative concentrations of that collagen type in glomeruli previously found to be normal or sclerotic were determined, as shown in the lower panel of FIG. 2.

The relative cell numbers in glomeruli of five patients without glomerular sclerosis (normal) were compared to five patients with sclerosis. As reflected in FIG. 3 the difference between the groups in glomerular relative cell number was not significant (p>0.8) whereas, for the $\alpha_2$IV collagen cDNA levels, the difference was statistically significant (0.01<p<0.025).

EXAMPLE 3

Relative Collagen mRNA Ratios in Glomeruli from Normal and Diseased Kidneys

Utilizing the methodology described in Examples 1 and 2, the relative ratios of $\alpha_2/\alpha_3$IV collagen mRNA were quantified in glomeruli taken from diagnostic biopsies of human patients with membranous glomerulonephritis (MN) and diabetic nephropathy (DM) and from nephrectomies with glomerulosclerosis (NX GS) and without glomerulosclerosis (NX N1). As reflected in FIG. 4, the $\alpha_2/\alpha_3$IV collagen mRNA ratios were significantly higher in DM and in NS GS than in NX N1. (**P=0.0002, *P=0.02).

EXAMPLE 4

In Vitro Studies with PPS

Study A
Experimental Design:

Normal mesangial cells (8) were plated in basal medium plus 20% fetal bovine serum (Gibco, Grand Island, N.Y.) in 24-well plates (Nunc, PGC Scientific Corp., Gaithersburg, Md.) at a density of 2–2.5 ×10$^4$ cells/well. At 24 hours the medium was discarded, cells were washed twice with PBS and incubated for 24–72 h in serum-free medium with 0.1% bovine serum albumin (RIA grade, Sigma). The medium was replaced with fresh basal medium plus 20% fetal bovine serum with or without 5–100 µg/ml of PPS or compared to standard heparin (100µg/ml). Cells of duplicate wells were trypsinized and counted in an Elzone® cell counter (Particle Data Inc., Elmhurst, IL) at days +3 and +5. In parallel wells, thymidine incorporation was determined by adding 1µCi/well of [$^3$H]thymidine ([methyl-$^3$H]thymidine); 2.0 Ci/mM; DuPont NEN, Boston, Mass.). Counts were determined at day 1 or at day 3.

Results:

At day one (24 hours) the maximum dose-response plateaued at 50 µg/ml (FIG. 5) whereas at day three the maximum inhibitory response was noted at 25 µg/ml (FIG. 6).

Comparison between no addition (control) and heparin (100 µg/ml) and PPS (100 µg/ml), reveals that on a molar basis PPS is roughly twice as potent as native heparin (FIG. 7). The responses are quite reproducible (the error bars are very tight).

A summary graph (FIG. 8) compares the effect of PPS added to serum to control cells which were exposed only to serum.

Study B

Normal mesangial cell layers were exposed to PPS (100µg/ml) for varying periods, and reverse-transcribed. mRNA levels were measured for selected molecules at day 1 and compared with the levels at days 3 and 5 (see FIG. 9). There were no changes in type IV collagen mRNA, type I collagen mRNA was substantially decreased, TGF-βmRNA was reduced by 50%, and the 92 kDa enzyme activity was increased by more than 50%. The control was β-actin, which was unchanged, consistent with the absence of proliferation in the treated cells.

EXAMPLE 5

Animal Studies with PPS

Experimental Design:

12–20 week old GH transgenic animals were identified by PCR analysis of detergent-extracted material from tail biopsies using specific primers for the bovine growth hormone cDNA that did not cross-react with the mouse GH sequence. Four GH mice were treated (2 for 2 weeks and 2 for 4 weeks) with oral PPS in the drinking water and four age-matched GH mice received tap water for the same duration. The amount of PPS in the drinking water (500 mg/ml) was calculated to give each mouse the equivalent of 50 mg of PPS per day.

Isolation of Glomeruli, and in situ Reverse Transcription:

Glomeruli were isolated by microdissection in the presence of RNase inhibitors. The left kidney was perfused with saline followed by a collagenase solution containing soluble RNase inhibitors. The lower pole was removed prior to collagenase perfusion and snap frozen on dry ice for zymography. After collagenase digestion, 40–60 glomeruli were isolated at 4° C. in presence of vanadyl ribonucleoside complex, for reverse transcription (RT). In situ RT was performed as above except that the glomeruli were freeze-thawed once in acetone dry ice and sonicated at 2° C. for 5 minutes in the presence of 2% Triton and 4 units/µl of human placental RNase inhibitor (Boehringer Mannheim, Indianapolis, Ind.), prior to the addition of the RT components. A Micro Ultrasonic Cell Disrupter (Kontes, Vineland, N.J.) was used to refrigerate the samples during sonication.

Standard and Competitive PCR Assays:

Primers for mouse $\alpha_1$ IV and $\alpha_1$ I collagen, $\alpha$ smooth muscle cell actin, $\beta$-actin, laminin B1 tenascin, 92 kDa metalloproteinase and 72 kDa metalloproteinase mRNAs, and for bovine growth hormone genomic DNA, were synthesized on a PCR-Mate (Applied Biosystems, Foster City, Calif.). The identity of each amplified product was verified by size and by restriction enzyme analysis. Primer specificity for mRNA was determined by omitting the reverse transcriptase enzyme. PCR was performed using the Gene-Amp DNA Amplification kit (Perkin Elmer Cetus, Norwalk, Conn.). cDNA derived from a pool of 40–60 glomeruli/ mouse was initially assayed by standard PCR, using the log-linear part of PCR amplification. This permitted a rapid, non-quantitative assessment of mRNA levels. Thereafter, competitive PCR assays were utilized to measure $\alpha_1$IV collagen, PDGF-B, $\alpha$ smooth muscle cell actin, $\beta$-actin, and laminin B1 cDNAs by constructing a cDNA mutant for each molecule, with a small internal deletion or a new restriction enzyme site. Analysis of PCR products was performed using a PDI densitometer loaded with the Quantity One® image analysis software. Competitive PCR assays were performed in duplicate or triplicate.

Statistical Analysis:

The unpaired Student's t test, with the Welch approximation method, was used for comparisons between groups and a P value $<0.05$ was considered significant. All data are expressed as mean $\pm$SEM.

Results:

FIG. 10 reflects the decrease in glomerular labeling index in PPS-treated mice (Control 0.97 $\pm$0.17%, PPS 0.64 $\pm$0.05%, p<0.05).

The gels showing the results of the competitive PCR assays with various collagen types, metalloproteinases, basement membrane glycoproteins, growth factors and actin proteins are depicted in FIGS. 11 and 12.

FIG. 13 shows that $\alpha_1$IV collagen mRNA was decreased by PPS treatment (Control 982 $\pm$106, PPS 738 $\pm$75, p<0.01) (attomoles/glomerulus).

FIG. 14 shown that laminin $B_1$ mRNA was decreased by PPS treatment (Control 1403 $\pm$453, PPS 861.5 $\pm$18.3, p=0.05) (attomoles/glomerulus).

FIG. 15 shows that PDGF-B mRNA was decreased by PPS treatment (Control 53.97 $\pm$17.21, PPS 28.9 $\pm$9.4, p<0.04).

FIG. 16 shows that TGF-$\beta$mRNA was decreased by PPS treatment (Control 181 $\pm$35.7, PPS 102.85 $\pm$21.61, p<0.05) (attomoles/glomerulus).

$\beta$-actin levels were essentially stable in the PPS treated mice, verifying that the decrease in the other factors was not a result of decreased cell proliferation.

The foregoing data, generated by scientifically validated experimental procedures, demonstrate the effectiveness of PPS in decreasing the synthesis of excess extra-cellular matrix collagen and certain cellular growth factors while increasing the activity of collagen degradation enzymes. These effects indicate that PPS should be highly effective in the clinical management and reversal of scarring-type CPVD.

It has thus been shown that there are provided methods and compositions which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the following claims:

1. A method of treating a mammalian patient suffering from a chronic progressive vascular disease (CPVD) characterized by scarring or fibrosis in an affected organ or vasculature, to halt the progress of the disease and cause the resolution of already-formed scarring or fibrotic lesions, said method consisting of the administration to the patient of a pharmaceutical composition containing an effective vascular disease treatment amount of pentosan polysulfate (PPS) or a pharmaceutically acceptable salt thereof.

2. A method according to claim 1 wherein said disease is selected from the group consisting of chronic progressive glomerular disease; progressive renal failure after renal transplantation; occlusion of shunts used to provide vascular access in patients with endstage renal disease being treated with hemodialysis; chronic small blood vessel diseases; recurrence of stenosis in patients who have undergone coronary bypass surgery; and diabetic retinopathy.

3. A method according to claim 2 wherein said disease is chronic progressive glomerular disease.

4. A method according to claim 1 wherein a sufficient amount of said pharmaceutical composition is administered to the patient to provide a total daily dosage of from about 50 to 1200 mg.

5. A method according to claim 4 wherein said daily dosage is from about 100 to about 600 mg.

6. A method according to claim 4 wherein said daily dosage is administered in one to four equally divided doses.

7. A method according to claim 1 wherein said pharmaceutical composition is an orally administered dosage form.

8. A method according to claim 7 wherein said dosage form is selected from the group consisting of conventional or sustained release tablets, coated tablets, capsules, caplets, lozenges, liquids and elixirs.

9. A method according to claim 7 wherein said dosage form includes at least one pharmaceutically acceptable inert ingredient.

10. A method according to claim 9 wherein said inert ingredient is a filler, binder, solvent, excipient or carrier.

11. A method according to claim 7 wherein said dosage form contains from about 50 to about 300 mg per unit of PPS or a pharmaceutically acceptable salt thereof.

12. A method according to claim 1 wherein said pharmaceutically acceptable salt is the sodium salt.

13. A method according to claim 12 wherein said composition is in the form of a gelatin capsule containing PPS sodium, microcrystalline cellulose and magnesium stearate.

14. A method according to claim 3 wherein said chronic progressive glomerular disease is diabetic-induced glomerulosclerosis.

* * * * *